US005512042A

United States Patent [19]
Montoya et al.

[11] Patent Number: 5,512,042
[45] Date of Patent: Apr. 30, 1996

[54] VENOUS BLOOD RESERVOIR WITH INCREASED LEVEL AND VOLUME SENSITIVITY

[75] Inventors: Jean P. Montoya; Scott I. Merz, both of Ann Arbor, Mich.

[73] Assignee: Michigan Critical Care Consultants, Inc., Ann Arbor, Mich.

[21] Appl. No.: 246,999

[22] Filed: May 20, 1994

[51] Int. Cl.⁶ .............................. A61M 1/00; A61M 1/10
[52] U.S. Cl. .................................. 604/4; 604/403
[58] Field of Search ............................. 73/323; 128/760, 128/767; 604/403, 318, 4–6

[56] References Cited

U.S. PATENT DOCUMENTS

| | | | |
|---|---|---|---|
| 4,515,589 | 5/1985 | Austin et al. | 604/122 |
| 5,282,783 | 2/1994 | Lindsay | 604/403 |
| 5,286,262 | 2/1994 | Herweck et al. | 604/318 |
| 5,380,314 | 1/1995 | Herweck et al. | 604/403 |

*Primary Examiner*—Randall L. Green
*Assistant Examiner*—Mark O. Polutta
*Attorney, Agent, or Firm*—Harness, Dickey & Pierce

[57] ABSTRACT

A blood reservoir which includes a primary reservoir that smoothly transitions into an outlet reservoir located beneath the primary reservoir. An inlet port permits the inflow of blood into the reservoir and an outlet port permits blood to flow out of the outlet reservoir. The primary reservoir defines an upper cavity that has first average cross sectional flow area. The outlet reservoir defines a lower cavity that has a second average cross sectional flow area which is preferably not more than one-half of the first average cross sectional flow area. The outlet reservoir therefore exhibits an increased sensitivity to blood level changes in the reservoir. The reservoir further includes features which inhibit the flow of blood from the outlet reservoir if the volume of blood in the outlet reservoir is reduced to a predetermined safety level.

16 Claims, 3 Drawing Sheets

VENOUS BLOOD RESERVOIR WITH INCREASED LEVEL AND VOLUME SENSITIVITY

STATEMENT OF GOVERNMENTAL SUPPORT

This invention was made with support from the U.S. Government under Grant No. 2R44 HL46613 awarded by the National Institutes of Health. The U.S. Government has certain rights in this invention.

BACKGROUND AND SUMMARY OF THE INVENTION

This invention generally relates to a venous and cardiotomy reservoir. More particularly, the invention relates to a venous and cardiotomy reservoir which incorporates an outlet reservoir that exhibits an enhanced sensitivity to the level or volume of blood in the reservoir outlet. The reservoir is particularly adapted for use with a collapsible peristaltic pump.

Reservoirs and pumps of the above general type have found particular utility in various medical fields for transferring bodily fluids and blood between a patient and one or more extracorporeal devices. Medical procedures which commonly employ peristaltic pumps and reservoirs include, without limitation, open heart surgery for circulating blood between a patient and a heart lung machine, dialysis procedures for transferring blood between a patient and dialyzer, and cardiopulmonary bypass (CPB) surgery where blood is removed from the open thoracic cavity, oxygenated and returned to the patient.

A collapsible peristaltic pump can also be used to advantageously control the liquid level in a reservoir upstream from the pump. This is achieved by strategically positioning the pump inlet at a height equal to the lowest allowable liquid level in the reservoir. Taking advantage of the hydrostatic pressure of the liquid in the reservoir, when the liquid level in the reservoir drops to the height equivalent of the pump inlet, the pump tubing will collapse and no further pumping will take place, even though the pumping mechanism itself may continue to operate.

During CPB surgery, blood is typically drawn from a venous blood vessel through a venous catheter into a venous reservoir. The blood is then pumped through an oxygenator, heater or other extracorporeal device and returned through an arterial catheter to an arterial blood vessel of the patient. The reservoir is often an open reservoir located between the patient and the inlet of the pump. An open reservoir is formed from a rigid container that is vented to ambient air. When blood enters the open reservoir it displaces a portion of the air in the reservoir while maintaining an air to blood interface. When provided in the CPB surgery blood circuit, the reservoir allows, among other things, storage of blood, elimination of air bubbles within the blood, filtering of the blood, defoaming of the blood, and controlling the amount of suction applied to the venous catheter. The amount of suction is typically limited by gently siphoning the venous blood via gravity into the open reservoir.

A potential hazard during CPB surgery is the emptying of the blood from the venous reservoir and the pumping of air into the patient. Emptying of the reservoir could occur if the flow rate out of the reservoir is higher than the venous drainage from the patient into the reservoir. Although the rate of venous drainage is not measured, it is the responsibility of the perfusionist (a technician trained to operate a heart/lung machine) to maintain a safe level of blood in the reservoir (usually 300 to 500 ml). The perfusionist must therefore adjust the pump speed to accommodate changes in the venous supply. Despite close control, the reservoir can quickly be emptied while the perfusionist is temporarily distracted and, consequently, air can be pumped into the patient. While electronic level sensors are commonly used to warn the perfusionist of a low blood level in the reservoir, these sensors can malfunction and fail.

Peristaltic pumps are volumetric pumps in which a rotating or linearly moving member uses rollers at spaced apart intervals to progressively compress a flexible tube and propel a fluid (e.g. blood) through the tube. The principal advantage of the peristaltic pump is its simplicity of operation and an absence of contact between the fluid and frictional surfaces, including valves, which can be responsible for a variety of hazards such as the hemolyzing of blood cells. Thus, instead of directly contacting the rotating member of the pump, the fluid only contacts the chemically inert tube. Another type of peristaltic pump is a collapsible peristaltic pump.

Collapsible peristaltic pumps utilize a tube which becomes completely occluded in its free condition (when the pressure within the tubing is equal to the pressure surrounding the outside of the tubing). Collapsible peristaltic pumps are described in U.S. Pat. Nos. 5,222,880 and 5,281,112, which are herein incorporated by reference. These types of pumps are advantageous because they inherently regulate output flow. Specifically, the output flow of the pump is dependent on the inlet pressure of the fluid into the pump. As a result of this feature, if the line upstream of the pump becomes occluded, emptied or otherwise fails to supply fluid to the pump, the tube of the pump will occlude and preventing the pump from generating dangerously low negative pressures. Such pressures can significantly hemolyze the blood and can empty the tissue vessel of the patient resulting in a collapse of the vessel and damage to the tissue itself.

With the above limitations in mind, it is an object of the present invention to provide a venous blood reservoir which can be used with a variety of peristaltic pumps including collapsible peristaltic pumps and which can be used in conjunction with a cardiotomy reservoir.

It is also an object of this invention to provide a reservoir which substantially eliminates the need for close control by a perfusionist over the blood level.

Another object of this invention is to provide a reservoir having a distinct outlet portion which has a greater sensitivity to changes in the level or volume of blood in the reservoir.

Yet another object of this invention is to provide a reservoir which incorporates a safety level defined as the level below which the liquid in the reservoir should not be allowed to go.

Another object of this invention is to provide a reservoir in which the level sensitive outlet portion of the reservoir is capable of containing a volume which is at least equivalent to the stroke volume of the pump with which it is used.

A further object of this invention is to provide a reservoir having an outlet portion whose height or level, when containing maximum volume, will provide a hydrostatic pressure sufficient to ensure at least a 50% maximum output by the pump.

Still another object of this invention is to provide a blood pumping system which incorporates a reservoir having a outlet portion of enhanced level sensitivity and used in conjunction with a collapsible peristaltic pump.

A further object of this invention is to provide a reservoir which includes a mechanism for preventing the outflow of blood from the reservoir when the blood level in the reservoir falls below a minimum acceptable level.

In achieving the above and other objects, the present invention provides for a venous blood reservoir which is defined as having a primary or upper portion or reservoir that smoothly transitions into an outlet or lower portion or reservoir. As suggested, the outlet reservoir is located beneath the primary reservoir. The primary reservoir defines an upper cavity and may include inlet ports which permit the inflow of blood into the reservoir. The blood is disposed into the reservoir at a location beneath the blood/air interface to prevent splattering of the blood and bubble formation. The outlet reservoir defines a lower cavity and includes an outlet port which permits the outflow of blood from the reservoir to the pump. The outlet reservoir has an average cross sectional flow area that is less than the average cross sectional flow area of the primary reservoir. Because of this difference in cross sectional flow area, the outlet reservoir has an increased sensitivity in exhibiting, in terms of blood level, changes in the blood volume. A perfusionist is therefore able to more readily detect the rate of change of the blood level in the outlet reservoir as compared to the rate of change of the blood level in prior reservoirs or even the primary reservoir of the present invention.

A safety level is also defined in the outlet reservoir. As further discussed below, this safety level defines that portion of the outlet reservoir which is to correspond in height to the inlet of the collapsible peristaltic pump. The volume of the outlet reservoir above the safety level is equal to at least one stroke volume of the pump to provide the perfusionist with a factor of safety as well as a visually determinable gauge as to the specific amount of blood left in the outlet reservoir. Since the output flow of a collapsible pump is dependent on the inlet pressure of the fluid into the pump, the highest level of the blood in the outlet reservoir is an amount sufficient to create a hydrostatic pressure that will generate at least a 50% maximum output of the pump. Thus when the level of blood is within the outlet reservoir, at or above the safety level, the perfusionist is therefore aware that the pump output flow may be seriously compromised.

The outlet of the present reservoir is connected by a conduit to the inlet of a collapsible peristaltic pump. As suggested above, the height of the inlet is set to correspond with the height of the safety level defined in the outlet reservoir, or vise versa. In this manner, when the level of blood in the outlet reservoir reaches the safety level, the pressure on the interior and exterior of the collapsible tube of the pump will be substantially equal causing the tube to occlude. This occlusion prevents the generation of negative pressures within the pump and the pumping of air into the patient. This occurs regardless of whether the transfer mechanism of the pump continues to operate or whether it is stopped.

In an alterative embodiment, the present invention includes a mechanism which operates in response to the level of blood in the outflow reservoir to prevent the outflow of blood from the reservoir once the level of blood therein reaches a critical or safety level. While in the prior embodiment this is achieved by a height adjustment of the outlet reservoir safety level relative to the inlet of the collapsible peristaltic pump, in the second embodiment a check valve or other mechanism is incorporated into the outlet reservoir. This enables the reservoir to be used not only with collapsible peristaltic pumps, but also with other pumps that do not generate significant negative pressures at their inlets.

Additional benefits and advantages of the present invention will become apparent to those skilled in the art to which the present invention relates from the subsequent description of the preferred embodiments and the appended claims, taken in conjunction with the accompanying drawings.

DETAILED DESCRIPTION OF THE PREFERRED EMBODIMENTS

Figure 1:
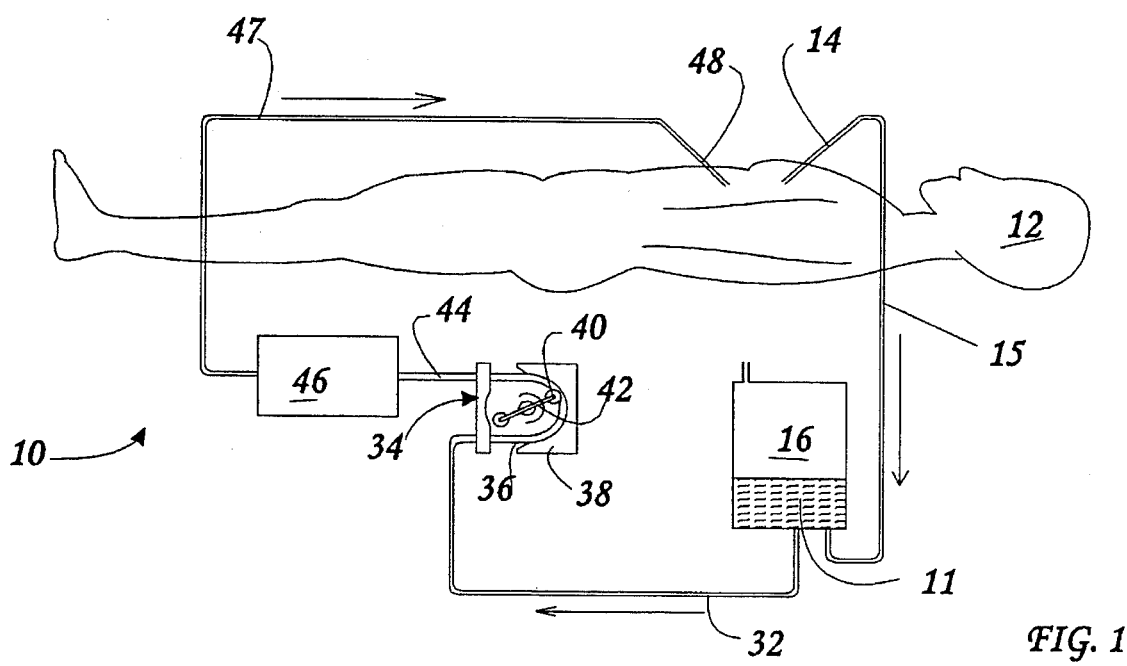
FIG. 1 is a diagrammatic illustration of a typical blood circuit for CPB surgery.

Referring now to the drawing, a typical blood circuit setup for cardiopulmonary bypass (CPB) surgery is generally illustrated in FIG. 1 and designated at 10. While the present invention is being described particularly in relation with the CPB surgery circuit, it should be understood that the invention will have utility in a wide variety of medical and non-medical procedures including, without limitation, open heart surgery and dialysis procedures.

During operation of the CPB surgery blood circuit 10, blood 11 is drawn from a venous blood vessel (not shown) of a patient 12 through a venous catheter 14 and medical grade flexible tubing 15 into an open venous reservoir 16. Typically, the blood 11 is gently siphoned under the influence of gravity from the patient 12 into the venous reservoir 16. Among other items, the reservoir 16 allows for the storage of blood 11, the elimination of air bubbles entrained in the blood 11, the filtering of the blood 11 and the defoaming of the blood 11. Additionally, the reservoir 16 can be used to control the amount of suction applied through the venous catheter 14 by increasing or decreasing the height of the reservoir 16 relative to the patient 12.

Figure 2:
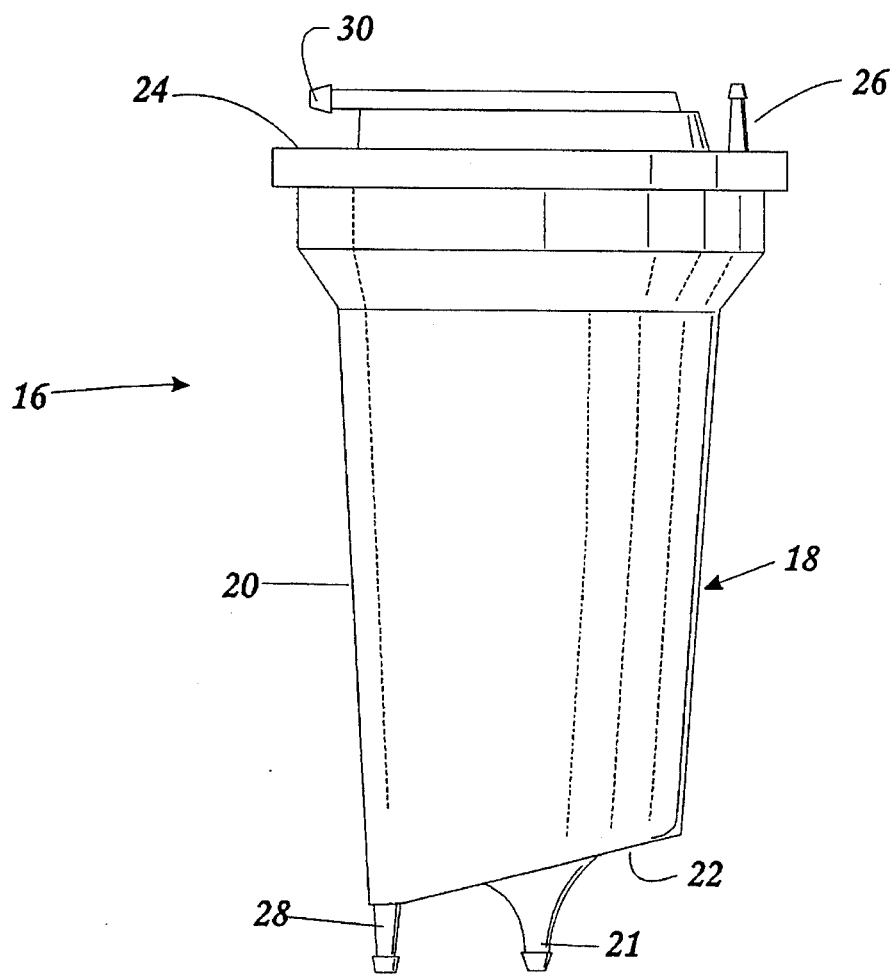
FIG. 2 is a perspective view of a venous and cardiotomy reservoir as is typically used in the blood circuit setup shown in FIG. 1.

As illustrated in FIG. 2, a typical venous and cardiotomy reservoir 16 includes a housing 18 which defines a cavity into which the blood 11 is received. The housing includes a side wall 20, a bottom wall 22 and a top wall 24. An inlet port 21, defined in the bottom wall 22, is adapted to receive the medical grade flexible tubing 15 leading from the venous catheter 14 and permit the flow of blood 11 into the reservoir 16. An outlet port 28 is defined in the bottom wall 22 and permits the outflow of blood 11 from the reservoir 16. The reservoir 16 may be further provided with additional inlet ports 30 and a vent 26 to enhance its operation and provide for other features and/or connections as may be required by the particular medical procedure in which the reservoir 16 is being used. Additional ports 30 may include filtered cardiotomy inlets, priming ports, and blood sampling ports.

Cardiotomy reservoirs are used to filter and store blood collected from the wound of the operating field. Typically, "free" blood in the wound area is removed through a suction tube and pumped into the cardiotomy reservoir. In the cardiotomy reservoir, the blood is filtered, stored and later drained into a main venous reservoir. The filtered cardiotomy blood is thus added to the circulating blood of the extracorporeal circuit. Recently, cardiotomy reservoirs have been integrated with the venous reservoir so that the blood can be immediately filtered and stored with the circulating blood.

The outlet port 28 connects a medical grade, flexible tube 32 to a peristaltic pump 34. The pump 34 itself includes a length of pump tube 36 which is curved and located within a race 38. To force fluid through the pump tube 36, at least two rollers 40 are rotated by a carrier 42. The rollers 40 engage and compress the pump tube 36 causing the movement of the blood through the pump 34 to another flexible tube 44 which delivers the blood to an oxygenator 46 or other extracorporeal device. Once the blood 11 has been oxygenated in the oxygenator 46, it is returned through a medical grade tubing 47 to an arterial catheter 48 into an arterial blood vessel of the patient 12.

One significant hazard which can occur during CPB bypass is that blood 11 can be emptied from the reservoir 16 resulting in the pumping or introduction of air through the blood circuit 10 into the patient 12. A situation where this could occur is when the flow rate out of the reservoir 16 is set above the venous drainage from the patient 12 into the reservoir 16. To maintain a safe level of blood 11 in the reservoir 16, a perfusionist must continuously adjust the speed of the pump 34 to accommodate changes in the flow rate of the venous drainage. This can prove difficult because the rate of blood level change in the reservoir 16 is hard to visually determine and distinguish. Despite close attention and control, the reservoir 16 can be quickly emptied if the perfusionist is temporarily distracted. While electronic blood level sensors have been used with reservoirs 16 to warn the perfusionist of a low blood level in the reservoir, these sensors can malfunction.

Figure 3:
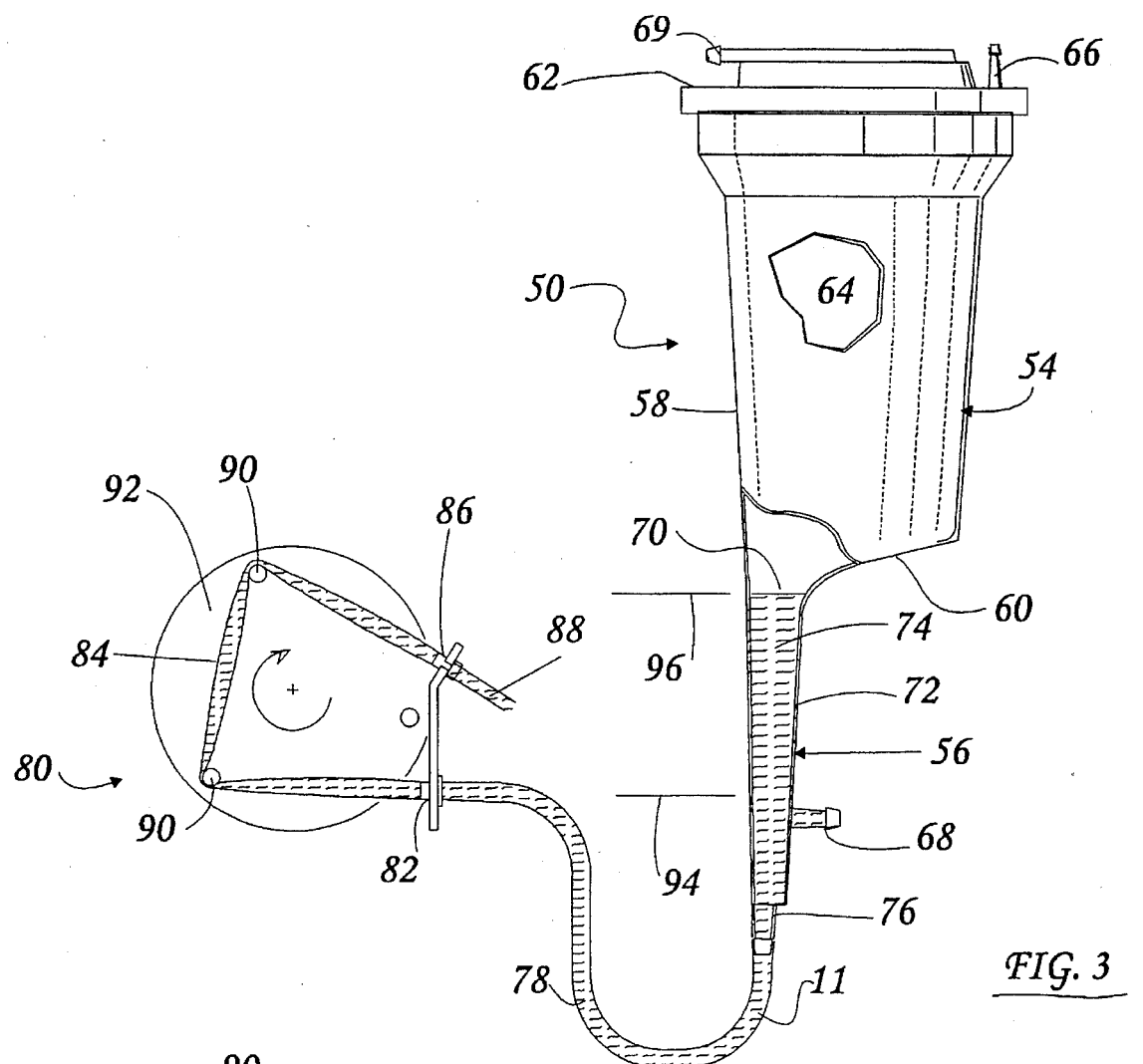
FIG. 3 is a diagrammatic illustration of a venous and cardiotomy system incorporating the principles of the present invention and shown when the reservoir and pump are operating at least a 50% maximum output.
Figure 4:
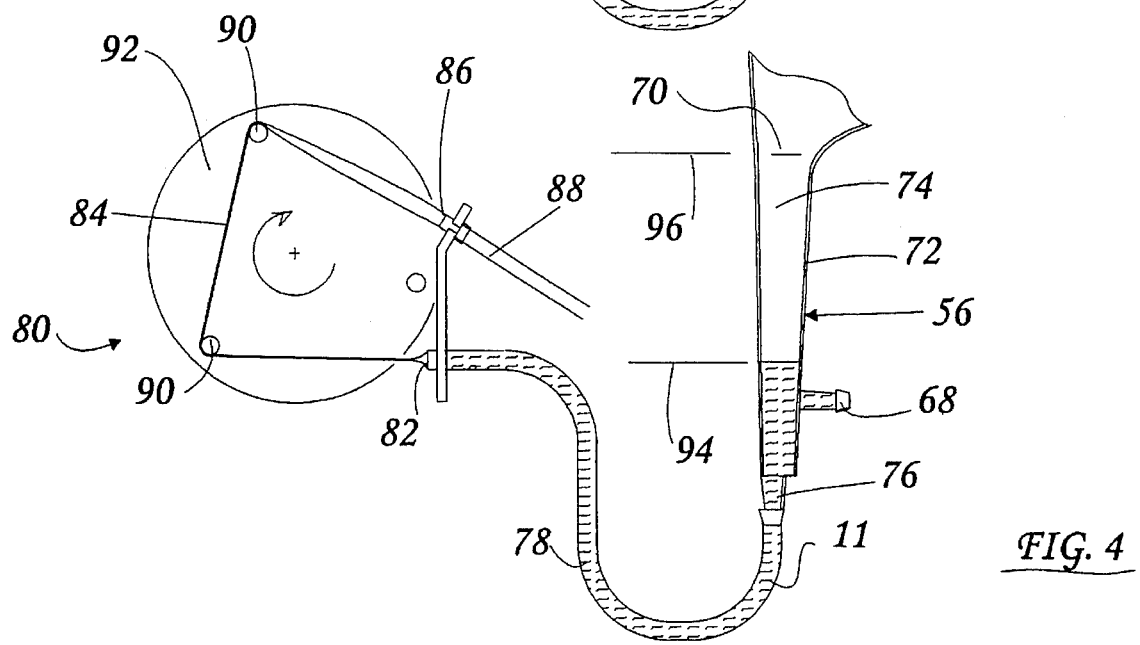
FIG. 4 is an illustration of the system shown in FIG. 3 except with the blood level in the outlet reservoir at the safety level and further illustrating the occlusion of the tubing in the collapsible peristaltic pump in response thereto.

Referring now to FIGS. 3 and 4, a venous reservoir 50 embodying the principles of the present invention is illustrated therein. While this reservoir 50 has some basic features common to the prior art, the significance of its distinguishing features will become more apparent in the discussion which follows.

The reservoir 50 itself may be rigid or flexible and includes a housing which is further defined into a primary or upper reservoir 54 and an outlet or lower reservoir 56. The primary reservoir 54 is constructed of a transparent or translucent material and is formed by side walls 58, a bottom wall 60 and a top wall 62 which cooperate to define an upper cavity designated at 64. A portion of the bottom wall 60 defines an outlet orifice 70. The outlet orifice 70 constitutes a smooth transition from the primary reservoir 54 into the outlet reservoir 56 so that a substantially laminar flow in the blood 11 is maintained as it is transferred from the primary reservoir 54 into the outlet reservoir 56.

The outlet reservoir 56 is similarly transparent or translucent and includes a side wall 72 which cooperates to define a cavity, designated as lower cavity 74, having an inlet port 68. The side wall 72 converges and terminates at its lower end in an outlet port 76.

The inlet port 68, connected to the venous catheter 14 by the tube 15, is defined in the outlet reservoir 56 so that blood 11 will flow into the reservoir 50 at a location beneath the lowest level of the air/blood interface that will occur in the reservoir 50. Preferably, the blood 11 will inflow through the inlet port 68 into the outlet reservoir 56 at a location beneath a safety level further discussed below. Alternative locations for the inlet port 68 could be employed as long as the actual inflow of blood occurs below the air/blood interface. For example, if located in the top wall 62 of the reservoir 50, the inlet port 68 could be connected via a tube inside the reservoir 50 to discharge in the bottom of the outlet reservoir 56. One or more additional inlet ports 69, which may include filtered cardiotomy and priming ports, and a vent 66 are also defined in the reservoir 50.

Since the inlet port 68 and the outlet port. 76 are relatively close to one another at the bottom of the reservoir 50, defoamers and screens (not shown) are used to prevent air bubbles entrained in the inflowing blood from passing directly to the outlet 76. Instead, the screens direct the bubbles upward toward the air/blood interface while blood is permitted to cross the screen to the outlet 76.

The outlet port 76 is coupled by a medical grade, flexible tube 78 to a peristaltic pump, designated at 80, which is generally of the collapsible variety. The tube 78 is connected to an inlet 82 of the pump 80 such that blood 11 can be transmitted from the tube 78 into a collapsible pump tube 84. The pump tube 84 is constructed so that when the pressure on the interior of the pump tube 84 is equal to the pressure on the exterior of the pump tube 84, the pump tube 84 will collapse, fully occlude and cause the pump 80 to stop pumping blood 11. This collapsed condition is referred to as the "free condition" of the pump tube 84. Because the pump tube 84 is occluded in its free condition, the collapsible peristaltic pump 80 requires a positive inlet pressure in order to operate. The pump 80 is therefore dependent upon the hydrostatic pressure of the in-flowing blood 11 to enable an outflow of blood 11 from the pump 80.

The pump 80 itself includes a set of rollers 90 which are rotated by a carrier 92 so as to engage the pump tube 84. As the rollers 90 close and occlude the tube 84, their movement causes the movement of the blood 11 through the pump 80. While the pump 80 will necessarily include additional control features, it is only schematically illustrated in the accompanying figures for the sake of clarity.

From the pump 84, the blood 11 is pumped through an outlet 86 to which is connected another flexible tube 88. The tube 88 is further connected to one or more extracorporeal devices, such as an oxygenator or heater 46, before transmitting the blood 11 back to the patient 12 through the tube 47 and the arterial catheter 48.

Specifically referring to the outlet reservoir 56, it can be seen that the outlet reservoir 56 has two level lines 94 and 96 defined thereon. The first and lower of these level lines defines a safety level 94 while the upper level 96 is generally defined at the height of the inlet orifice 70 from the primary reservoir 54. The outlet reservoir 56 has an average horizontal cross sectional flow area which is less than the average cross sectional flow area defined by the primary reservoir 54. Preferably, the average cross sectional flow area of the outlet reservoir 56 is less than ½ and, more preferably, less than ¼ the average cross sectional flow area of the primary reservoir 54. This difference in cross sectional flow area provides the outlet reservoir 56 with a heightened visible sensitivity to the rate of change of blood 11 therein. Accordingly, a small change in the volume of blood 11 will demonstrate a greater change in blood level in the outlet reservoir 56 than the same rate of change will exhibit in the primary reservoir 54. This more readily enables a perfusionist or other technician to determine when the blood level is too low and, when connected to a suction pump, when the output of the pump 80 is too great for the venous drainage into the reservoir 50.

When the level of the blood 11 is at the upper level 96 indicator of the outlet reservoir, a sufficient hydrostatic pressure is generated to produce at least a 50% maximum output from the collapsible peristaltic pump 80. This is significant because the perfusionist is assured that the collapsible pump 80 flow rate will not be seriously compromised as long as the level is equal or above the level indicator 96. Obviously, when the blood level falls below upper level 96, the pump 80 flow rate drops as the hydrostatic pressure falls. Additionally, the volume of the outlet reservoir 56 defined between the upper level 96 and the safety level 94 is at least equal to one stroke volume (the volume of blood 11 capable of being captured within the tube 84 between two successive rollers 90) of the collapsible peristaltic pump 80. This is significant in preventing the entire volume of the outlet reservoir from being emptied and air being pumped in a single stroke of the collapsible pump 80. Since the pump 80 can properly operate with the blood level being between the upper level 96 and the safety level 94, the blood volume contained in the outlet reservoir is usable by the pump 80 when the primary reservoir 54 is empty and is therefore a working volume of blood to the pump 80. The safety level 94 accordingly defines the minimum operating blood level as further discussed below.

The design of the proposed reservoir 50 coupled with a collapsible peristaltic pump 80 enables the pump 80 to be used to control the level of blood 11 in the reservoir 50. This is achievable if the pump inlet 82 is strategically positioned at a height level equal to the lowest allowable blood level, the safety level 94, in the outlet reservoir 56. Set up in this manner, when the blood level in the outlet reservoir 56 drops to the safety level 94, the resulting hydrostatic pressure causes the pump tube 84 to collapse and occlude thereby preventing any further pumping of the blood 11 by the collapsible peristaltic pump 80. When occluded, no further pumping can take place even though the pump 80 continues to operate. The carrier 92 and rollers 90 of the collapsible peristaltic pump 80 can continue to operate without fear that negative pressures will be generated within the pump tube 84, possibly hemolyzing the blood 11, or that all of the blood 11 in the reservoir 50 will be drawn out of the outlet reservoir 56 causing air to be pumped into the patient 12.

As can be seen from the above, the proposed reservoir 50, coupled with a collapsible pump 80, substantially eliminates the need for close control over the venous reservoir blood level by the perfusionist. The pump 80 acts as an automatic controller of flow because of its dependency on the blood level in the outlet reservoir 56. As the blood level in the outlet reservoir 56 decreases toward the safety level 94, the filling pressure of the pump is reduced resulting in the pump tube 84 filling with less blood. This occurs until the pump 80 eventually stops filling and occludes.

Figure 5:
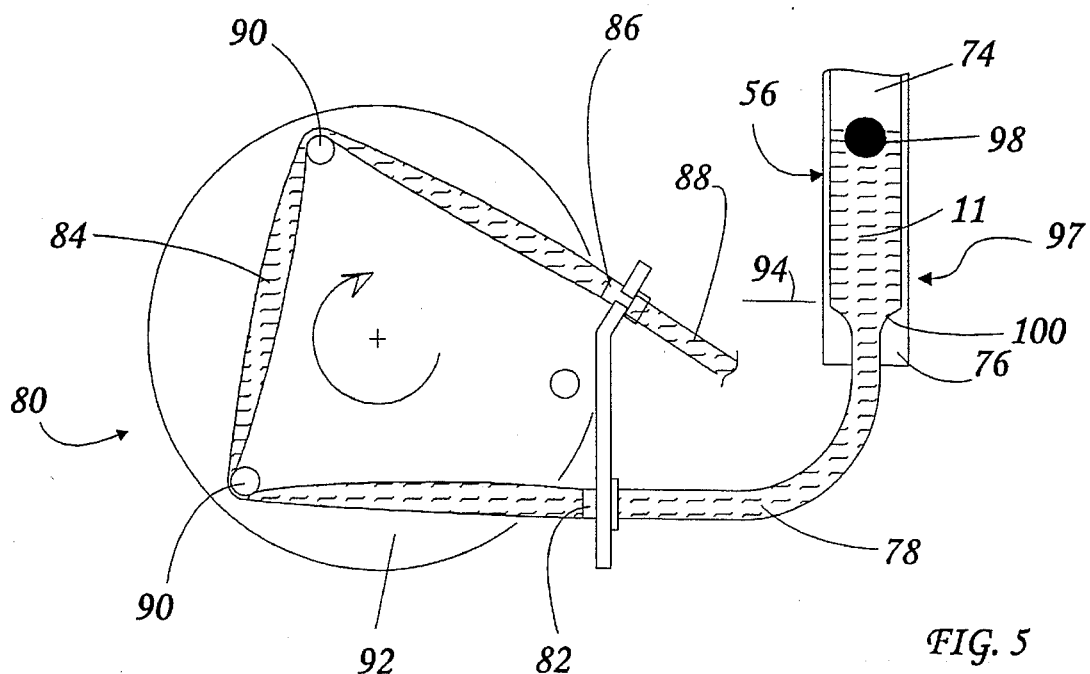
FIG. 5 is a diagrammatic illustration of a second embodiment of the present invention in which a check valve is incorporated into the outlet reservoir to allow for different relative height positioning of the outlet reservoir and the pump while still preventing the outflow of blood from the outlet reservoir when the level therein drops to the safety level.
Figure 6:
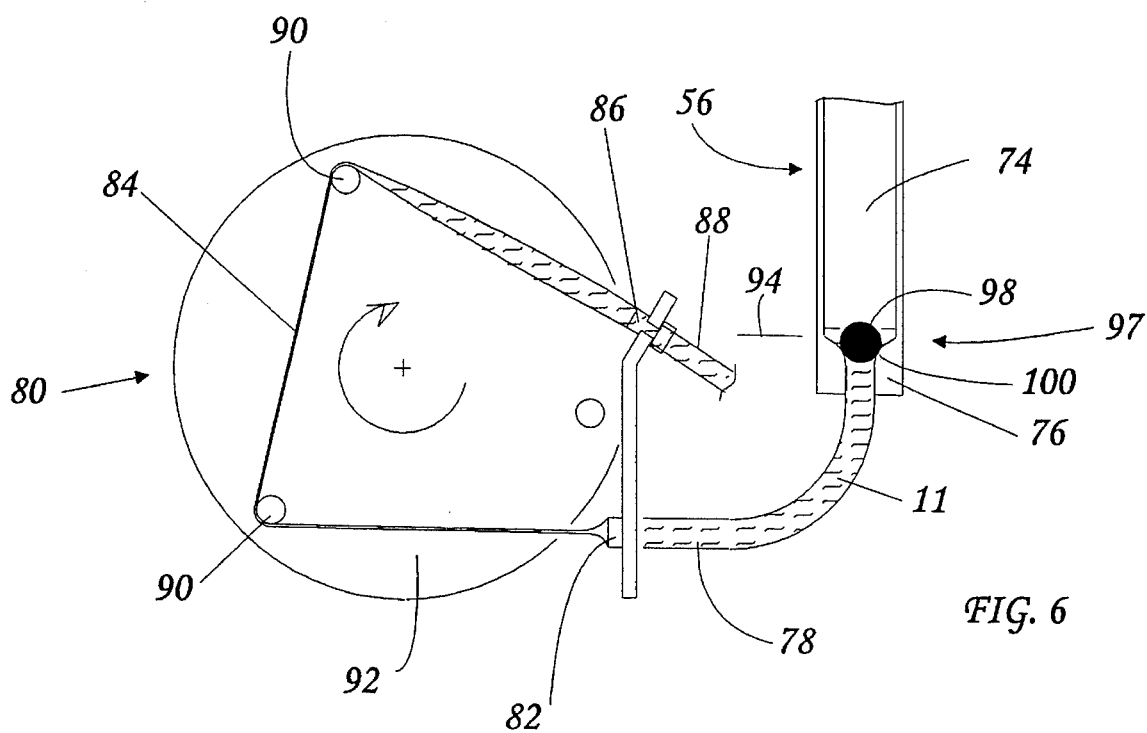
FIG. 6 is a view similar to that seen in FIG. 5 but illustrating the check valve being engaged as a result of the blood level dropping to the safety level and further illustrating the occlusion of the tubing of the pump in response thereto.

Referring now to FIGS. 5 and 6, a second embodiment of the present invention is illustrated therein. In the second embodiment, the reservoir 50, and in particular the outlet reservoir 56, incorporates a positive stop mechanism 97 that prevents emptying of the blood 11 out of the outlet reservoir 56. This second embodiment is advantageous because it permits the inlet 82 of the collapsible peristaltic pump 80 to be located at a height which does not correspond to the height level of the safety level 94 of the outlet reservoir 56. While only one stop mechanism 97 is illustrated herein, it should be understood that numerous alternative positive stop mechanisms 97 can be employed with equal success and that the stop mechanism 97 could be employed with a non-collapsible pump or with a reservoir lacking an outlet reservoir 56 as described above.

To provide the reservoir 50 with a positive stop mechanism 97, a check valve is incorporated into the lower end of the outlet reservoir 56. As seen in FIGS. 5 and 6, as the level of blood 11 in the outlet reservoir 56 decreases, a ball float 98 progresses toward a seat 100 defined by the outlet port 76. The shape of the seat 100 conforms to the ball float 98 so that when they are engaged, the blood 11 and air is prevented from being further drained out of the reservoir 50. Because the ball float 98 will prohibit blood 11 from being drained from the outlet reservoir 56 once the blood level reaches the level defined by the seat 100, the safety level 94 and the outlet port 76 can be positioned above the inlet 82 of the pump 80. The buoyancy and the size of the float, as well as the geometry of the outlet reservoir 56 itself, determines the volume of blood 11 which will remain in the reservoir 56 when the check valve 97 closes.

Obviously, this type of valved reservoir 50 can only be used in conjunction with a pump that will not create a significant negative or suction pressure which might result in cavitation and damage to the blood located between the closed valve and the pump. A collapsible peristaltic pump 80 having a fully occlusive tube 84, or with only a mildly biased tube 84, is ideal for this application. Other varieties of pumps would require additional pressure controls increasing the costs of the system. The stop mechanism 97 could however be used with other types of reservoirs, including those without the outlet reservoir 56 described above.

While the above description constitutes the preferred embodiments of the present invention, it will be appreciated that the invention is susceptible to modification, variation and change without departing from the proper scope and fair meaning of the accompanying claims.

What is claimed is:

1. An apparatus for preventing the emptying of blood from a blood reservoir, said apparatus comprising:

a blood pump having a predetermined stroke volume;

a housing adapted to receive blood, said housing including side walls defining a primary reservoir which smoothly transitions into an outlet reservoir, said housing further including portions defining an inlet port permitting the inflow of blood into said reservoir and an outlet port permitting the outflow of blood out of said reservoir, said outlet port defined in said outlet reservoir;

said primary reservoir further defining an upper cavity adapted to receive and contain a first volume of blood therein, said upper cavity having a first average cross sectional flow area; and said outlet reservoir exhibiting an increased sensitivity over said primary reservoir to blood level changes therein, said outlet reservoir defining a lower cavity having an upper level and a lower level adapted to receive and contain a second volume of blood therebetween, said second volume of blood being less than said first volume of blood, said lower cavity having a second average cross sectional flow area which is less than said first average cross sectional flow area, said second volume of blood constituting a working volume usable by the blood pump when said primary reservoir is empty and being equal to at least one stroke volume of the blood pump, said lower level defining a minimum level of blood for use with the blood pump and said outlet reservoir including prevention means for preventing the outflow of blood from said reservoir when the level of blood in said outlet reservoir is at or below said safety level.

2. A blood reservoir as set forth in claim 1 wherein said second average cross sectional flow area is not more than one-half said first average cross sectional flow area.

3. A blood reservoir as set forth in claim 1 wherein said second average cross sectional flow area is not more than one-fourth said first average cross sectional flow area.

4. A blood reservoir as set forth in claim 1 wherein said prevention means includes a check valve located in said outlet reservoir.

5. A blood reservoir as set forth in claim 4 wherein said check valve is a ball check valve.

6. A blood reservoir as set forth in claim 1 wherein said second volume of blood is of an amount producing a sufficient hydrostatic pressure for at least a fifty percent maximum output from the pump.

7. A blood reservoir as set forth in claim 1 wherein said primary reservoir exhibits a taper converging generally at said outlet reservoir and said outlet reservoir exhibits a taper converging at said outlet port.

8. A blood reservoir as set forth in claim 1 wherein said housing is rigid.

9. A blood reservoir as set forth in claim 1 wherein said housing is flexible.

10. A blood reservoir as set forth in claim 1 wherein said inlet port is formed in said reservoir such that the inflow of blood into said reservoir occurs beneath the level of the air/blood interface in said reservoir.

11. A blood reservoir as set forth in claim 1 wherein said inlet port is formed in said outlet reservoir such that the inflow of blood into said reservoir is generally beneath the level of the air/blood interface in said reservoir.

12. The apparatus of claim 1 wherein said lower level defines a safety level below which the outflow of blood from said reservoir to the pump is prevented.

13. The apparatus of claim 1 wherein said blood pump is a collapsible pump.

14. An apparatus for preventing emptying of a blood reservoir comprising:

a collapsible peristaltic pump including a frame, a plurality of rollers, carrier means for carrying said rollers in spaced apart relation along a predetermined path, and a pump conduit having an inlet end, an outlet end and a passageway defined therethrough, said conduit being at least partially collapsible to fully occlude at least a portion of said passageway in a free condition where pressure within said passageway is substantially equal to pressure acting on the outside of said conduit, said conduit being at least partially inflated and said passageway being open where pressure within said passageway is greater than pressure acting on the outside of said conduit;

a blood reservoir including an inlet port permitting the inflow of blood into said reservoir and an outlet port permitting the outflow of blood from said reservoir, said reservoir further including a primary reservoir which smoothly transitions into an outlet reservoir located beneath said primary reservoir, said primary reservoir defining an upper cavity having a first average cross sectional flow area and adapted to receive and contain a first volume of blood therein, said outlet reservoir defining a lower cavity having a second average cross sectional flow area which is not more than one-half of the first average cross sectional flow area, said lower cavity having an upper level and a lower level adapted to receive and contain a second volume of blood therein which is less than said first volume of blood, said second volume of blood being a working volume usable with said pump when said primary reservoir is empty, said outlet reservoir thereby exhibiting an increased sensitivity to changes of blood volume therein relative to said primary reservoir as a result of said second average cross sectional flow of said outlet reservoir, said lower level defining said predetermined safety level below which operation of said pump is prevented;

a connecting length of conduit coupled between said outlet port and said inlet end of said pump conduit; and blood flow stop means for stopping the flow of blood out of said reservoir to said pump when the volume of blood in said outlet reservoir reaches said safety level.

15. An apparatus for preventing emptying of a blood reservoir as set forth in claim 14 wherein said blood flow stop means includes means for locating the height of said safety level in said outlet reservoir so as to correspond to the height of said inlet end of said pump conduit.

16. An apparatus for preventing emptying of a blood reservoir as set forth in claim 14 wherein said blood flow stop means includes a check valve located in said reservoir.

* * * * *